(12) United States Patent
Wang et al.

(10) Patent No.: US 9,835,776 B2
(45) Date of Patent: Dec. 5, 2017

(54) MULTI-FACET DISPLAY DEVICE

(71) Applicants: BOE Technology Group Co., Ltd., Beijing (CN); Beijing BOE Optoelectronics Technology Co., Ltd., Beijing (CN)

(72) Inventors: Jiaheng Wang, Beijing (CN); Feng Bai, Beijing (CN); Jiuxia Yang, Beijing (CN)

(73) Assignees: BOE Technology Group Co., Ltd., Beijing (CN); Beijing BOE Optoelectronics Technology Co., Ltd., Beijing (CN)

( * ) Notice: Subject to any disclaimer, the term of this patent is extended or adjusted under 35 U.S.C. 154(b) by 100 days.

(21) Appl. No.: 14/787,600

(22) PCT Filed: Jun. 5, 2015

(86) PCT No.: PCT/CN2015/080831
§ 371 (c)(1),
(2) Date: Oct. 28, 2015

(87) PCT Pub. No.: WO2016/090871
PCT Pub. Date: Jun. 16, 2016

(65) Prior Publication Data
US 2016/0170100 A1      Jun. 16, 2016

(30) Foreign Application Priority Data
Dec. 12, 2014   (CN) .......................... 2014 1 0773851

(51) Int. Cl.
*H05K 5/00*  (2006.01)
*G02B 5/04*  (2006.01)
(Continued)

(52) U.S. Cl.
CPC ............... *G02B 5/04* (2013.01); *A61B 5/01* (2013.01); *A61B 5/14532* (2013.01);
(Continued)

(58) Field of Classification Search
CPC ....... G02B 5/04; G06F 1/1601; G06F 1/1626; G06F 1/1637; G06F 1/1647;
(Continued)

(56) References Cited

U.S. PATENT DOCUMENTS 6,495,262 B2 * 12/2002 Igeta .................. H01J 11/48
                                                    349/153
9,086,787 B2 *  7/2015 Park .................... G06F 3/0488
(Continued)

FOREIGN PATENT DOCUMENTS

CN        2378796 Y      5/2000
CN        1558280 A     12/2004
(Continued)

OTHER PUBLICATIONS

Sep. 30, 2016—(CN)—First Office Action Appn 201410773851.X with English Tran.
(Continued)

*Primary Examiner* — Hung S Bui
(74) *Attorney, Agent, or Firm* — Banner & Witcoff, Ltd.

(57) ABSTRACT

A multi-facet display device. The multi-facet display device comprises: a first display panel with a U-shaped structure and a second display panel with a planar structure. The first display panel comprises a display region with a planar structure, and two opposed side surfaces each connected with the display region via an arc surface. The two side surfaces of the first display panel are bonded with the two side edges of the second display panel to form a closed structure having an outer surface as a display surface of the multi-facet display device. Compared with a multi-facet
(Continued)

display device composed of multiple planar display panels, the multi-facet display device according to present invention can improve image continuity across respective display directions.

20 Claims, 4 Drawing Sheets

(51) Int. Cl.
*G06F 1/16* (2006.01)
*A61B 5/00* (2006.01)
*A61B 5/01* (2006.01)
*A61B 5/145* (2006.01)

(52) U.S. Cl.
CPC .......... *A61B 5/7445* (2013.01); *G06F 1/1601* (2013.01); *G06F 1/1626* (2013.01); *G06F 1/1637* (2013.01); *G06F 1/1647* (2013.01); *G06F 1/1652* (2013.01); *A61B 2560/0462* (2013.01)

(58) Field of Classification Search
CPC ..... G06F 1/1652; A61B 5/01; A61B 5/14532; A61B 2560/0462
USPC ................................. 361/728–730, 752, 800
See application file for complete search history.

(56) References Cited

U.S. PATENT DOCUMENTS

| | | | | |
|---|---|---|---|---|
| 9,189,016 B2* | 11/2015 | Jang | ...................... | G06F 1/1652 |
| 9,389,688 B2* | 7/2016 | Tossavainen | ........... | G06F 3/016 |
| 9,531,853 B2* | 12/2016 | Chuang | ............... | H04M 1/0266 |
| 2009/0318185 A1* | 12/2009 | Lee | ................... | H04M 1/72527 455/550.1 |
| 2012/0252534 A1* | 10/2012 | Kim | ........................ | H04M 1/22 455/566 |
| 2013/0002133 A1* | 1/2013 | Jin | ........................ | H01L 51/524 313/511 |
| 2013/0300697 A1* | 11/2013 | Kim | ....................... | G06F 1/1626 345/173 |
| 2014/0132488 A1* | 5/2014 | Kim | ........................ | H01L 51/52 345/76 |
| 2014/0320435 A1* | 10/2014 | Modarres | .............. | G06F 3/0412 345/173 |
| 2016/0029896 A1* | 2/2016 | Lee | .......................... | A61B 5/01 600/474 |
| 2016/0242702 A1* | 8/2016 | Wang | ..................... | G02F 1/133 |

FOREIGN PATENT DOCUMENTS

| | | |
|---|---|---|
| CN | 201259587 Y | 6/2009 |
| CN | 101965604 A | 2/2011 |
| CN | 102445774 A | 5/2012 |
| CN | 102855821 A | 1/2013 |
| CN | 103176304 A | 6/2013 |
| CN | 104460089 A | 3/2015 |
| CN | 204241802 U | 4/2015 |
| GB | 2176040 A | 12/1986 |
| KR | 20090089727 A | 8/2009 |

OTHER PUBLICATIONS

Feb 3, 2017—(CN) Second Office Action Appn 201410773851.X with English Tran.

Jul 28, 2015—International Search Report and Written Opinion Appn PCT/CN2015/080831 with English Tran.

Jul. 10, 2017—(CN) Third Office Action Appn 201410773851.X with English Tran.

* cited by examiner

MULTI-FACET DISPLAY DEVICE

The application is a U.S. National Phase Entry of International Application No. PCT/CN2015/080831 filed on Jun. 5, 2015, designating the United States of America and claiming priority to Chinese Patent Application No. 201410773851.X filed on Dec. 12, 2014. The present application claims priority to and the benefit of the above-identified applications and the above-identified applications are incorporated by reference herein in their entirety.

FIELD

The present invention relates to a multi-facet display device.

BACKGROUND

With the extension of the application area of display device, the display device is no longer limited in the demand for flat panel display. The demand for a multi-facet display device design has already existed nowadays. Such multi-facet display device generally comprises multiple flat display panels assembled together with each panel displaying in a respective direction. The multi-facet display device may be, for example, a light box. The images displayed on respective display panels of such multi-facet display device are independent with respective to each other. There are sharp edges and corners located at the joint of adjacent display panels, which makes it impossible to achieve image continuity among respective directions.

SUMMARY

In view of the above, the embodiments of present invention provide a multi-facet display device for achieving a continuous image display.

Therefore, the embodiments of present invention provide a first display panel with a U-shaped structure, the first display panel comprising a display region with a planar structure and two opposed side surfaces each connected with the display region via an arc surface; and a second display panel with a planar structure. The two side surfaces of the first display panel are bonded with two side edges of the second display panel to form a closed structure having an outer surface as a display surface of the multi-facet display device.

In one possible implementation, the multi-facet display device according to the embodiments of present invention further comprises: a first encasing plate closing a top of the closed structure; and a second encasing plate closing a bottom of the closed structure.

In one possible implementation, the first display panel is bonded with the second display panel, the first display panel is bonded with the first package plate, the first display panel is bonded with the second package plate, and the second display panel is bonded with the second package plate, and the bonding is made by a method comprising pressing or adhering matching recesses and protrusions on respective parts, or screwing.

In one possible implementation, the two side surfaces of the first display panel and the two side edges of the second display panel are assembled via a third encasing plate respectively.

In one possible implementation, the third encasing plate, the first encasing plate and the second encasing plate are in an integral structure.

In one possible implementation, the multi-facet display device according to the embodiments of present invention further comprises at least one function slot and/or physical function button disposed on at least one side surface of the first display panel; or disposed at a non-display region of the first display panel and/or the second display panel; or disposed on a surface of the first encasing plate and/or the second package plate.

In one possible implementation, said multi-facet display device according to the embodiments of present invention further comprises a health monitoring unit disposed on at least one side surface of the first display panel; or disposed at a non-display region of the first display panel and/or the second display panel; or disposed on a surface of the first encasing plate and/or the second package plate.

In one possible implementation, the health monitoring unit is an infrared detection unit for monitoring body temperature and/or minimal invasive detection unit for monitoring blood sugar level.

In one possible implementation, the first display panel and the second display panel are at least frameless at joints between the side surfaces of the first display panel and side edges of the second display panel.

In one possible implementation, the multi-facet display device according to the embodiments of present invention further comprises a circuit board connected with the display surface of the multi-facet display device through a flexible electronic skin.

In one possible implementation, the multi-facet display device according to the embodiments of present invention further comprises a transparent prism structure at least disposed at joints between the side surfaces of the first display panel and side edges of the second display panel, the transparent prism structure being configured for changing directions of emitting lights.

In one possible implementation, the transparent prism structure at least partially protrudes out of the outer surface of the closed structure, and has an arc or trapezoid cross sectional shape on a cross section which is perpendicular to the outer surface of the closed structure.

In one possible implementation, the first display panel is a LCD display panel, an OLED display panel or an electronic paper display panel; the second display panel is a LCD display panel, an OLED display panel or an electronic paper display panel.

In one possible implementation, the first display panel and the second display panel are touch control display panels.

In the multi-facet display device according to the embodiments of present invention, the two opposed side surfaces of first display panel bend toward the back of display region respectively, so that the first display panel forms a U-shaped structure. The two opposed side surfaces of first display panel bending toward the back of display region are assembled with the two side edges of second display panel respectively to form a closed structure. The display surface of the multi-facet display device is the outer surface of the closed structure. In the multi-facet display device according to the embodiments of present invention, the first display panel with the bending structure and the planar second display panel are assembled in a closed structure so that the function of displaying image can be achieved on the surfaces in at least four directions of the closed structure. The display surfaces of the first display panel with U-shaped structure in three directions are connected as a curved surface via the arc surfaces. Compared with the multi-facet display device consisted of multiple planar display panels, the multi-facet display device according to present invention improve image continuity across respective display directions.

BRIEF DESCRIPTION OF THE DRAWINGS

In order to describe the technical solutions in the embodiments of the present invention more clearly, accompanying drawings used in the description will be described briefly. It is apparent that the drawings mentioned in the following description are only some embodiments of the present invention, and various other drawings can be obtained by those of ordinary skilled in the art without creative labor based on these drawings mention above.

DETAILED DESCRIPTION

The technical solution of the embodiments of the present disclosure will be described clearly and fully in connection with the drawings of the embodiments of the present disclosure. It is obvious that the described embodiments are just a part but not all of the embodiments of the present disclosure. Based on the described embodiments of the present disclosure, those skilled in the art can obtain all other embodiment without any inventive work, which all fall into the scope of the claimed invention.

Unless otherwise defined, technical terms or scientific terms used herein shall have a common meaning known by those skilled in the art of the present disclosure. Words and expressions such as "first", "second" and the like used in the description and claims of the patent application of the present disclosure do not denote any sequence, quantity or significance, but distinguish different components. Likewise, words such as "a", "an" and the like do not denote quantitative restrictions, but denote the presence of at least one. Words such as "connected", "connecting" and the like are not restricted to physical or mechanical connections, but may include electrical connections, regardless of direct or indirect connections. Words such as "up", "below", "left", "right", etc., are only used to denote the relative positional relationship. In a case where the absolute position of the described object changes, the relative positional relationship change correspondingly.

Figure 1:
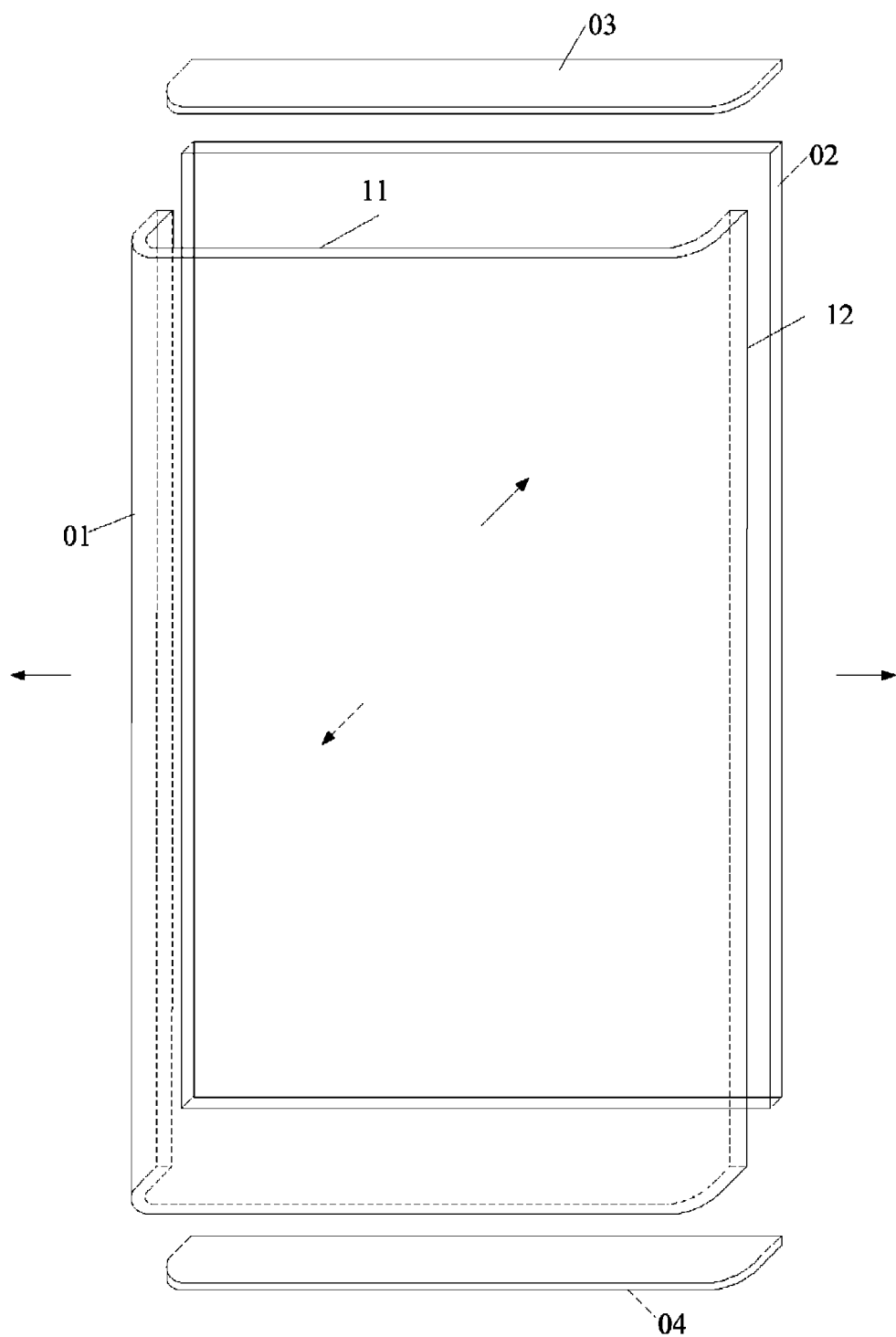
FIG. 1 is a structure exploded view of respective components in a multi-facet display device according to an embodiment of present invention.

The embodiments of present invention provide a multi-facet display device, as illustrated in FIG. 1. The multi-facet display device includes a first display panel 01 and a second display panel 02.

The first display panel 01 has a U-shaped structure including a planar display region 11 and two opposed planar side surfaces 12, and the each side surfaces 12 is connected with the display region 11 via an arc surface respectively.

The two side surfaces 12 of the first display panel 01 are assembled with the two side edges of second display panel 02 to form a close structure. As illustrated in the top view of FIG. 2, the multi-facet display device has a display region which is the outer surface of the closed structure, as indicated by hatching lines in FIG. 3

In the above multi-facet display device according to the embodiments of present invention, the U-shaped first display panel 01 and the planar second display panel 02 are assembled in a closed structure. It can be seen from FIG. 1, the closed structure includes four planar surfaces and two arc surfaces, and the images can be displayed on four planar surfaces in at least four directions (front, back, left, and right) and the two arc surfaces of the closed structure. In the first display panel 01 with the bending U-shaped structure, the display surface in three directions (front, left and right) are connected as a curved surface via the arc surfaces. In comparison with the multi-facet display device composed of multiple planar display panels assembled together with sharp edges and corners at the joint, the multi-facet display device according to the embodiments of present invention can improve the image continuity displayed across respective directions. It is noted that in FIG. 1, the upward arrows represent the back surface of the closed structure, the downward arrows represent the front surface of the closed structure, the leftward arrows represent the left surface of the closed structure, and the rightward arrows represent the right surface of the closed structure.

Figure 2:
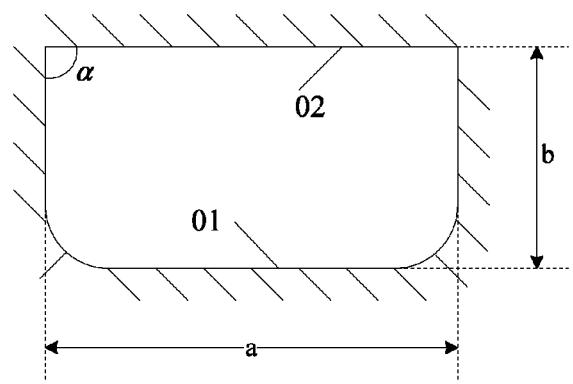
FIG. 2 is a top view of a multi-facet display device according to an embodiment of present invention.

As illustrated in FIG. 2, the ratio between the length b and length a of the adjacent planar surfaces of the multi-facet display device can be adjusted according to the applications of the multi-facet display device, so that the external profile of the multi-facet display device approximates a columnar structure with either a rectangular cross section or a columnar structure with a square cross section. In a case where the multi-facet display device is used for display in mobile terminals such as cell phones, the front and back surfaces can be designed to have a large area, and the left and right side surfaces can be designed to be narrow, which facilitates the ultra-thin design of mobile terminals. Furthermore, the essential components of mobile terminals such as the power source and circuit board can be placed within the closed structure of the multi-facet display device, so that the outer surface of the mobile terminals forms an integral image displaying surface. In a case where the multi-facet display device is applied to the 3D multi-facet display such as a stereo display wall, the area of the front and back surfaces can be designed substantially the same as that of the left and right side surfaces, and further details will not be described herein.

Furthermore, the angles between the adjacent planar surfaces of the multi-facet display device can be adjusted according to specific application. Generally, in order to achieve a good image continuity across respective display surfaces of the multi-facet display device, the angle is chosen as an obtuse angle or a right angle. For example, the angle can be a right angle shown in FIG. 2.

In actual implementations, the above multi-facet display device according to the embodiments of present invention can have at least one display surface designed as a main display surface according to the specific application. For example, in a case where the display device is applied to a cell phone, the front and back surfaces can be designed as main display surfaces with exemplary operation modes described as below.

1. The same content can be displayed on multiple main display surfaces simultaneously. For example, the front surface and back surfaces can display a same image simultaneously.

2. Different contents can be displayed on multiple main display surfaces. For example, the front surface can display a front image of a human body, whereas a back surface can display a back image of the human body.

3. The content is only displayed on one of the main display surfaces, whereas other main display surfaces are in power-off state.

Furthermore, in the above multi-facet display device according to the embodiments of present invention, some function buttons or UI icons of APP software can be displayed on the display surfaces other than the main display surfaces based on particular setting. For example, the function buttons can be displayed on the left surface, right surface, the curved transition surface connecting the left surface with the front surface, or the curved transition surface connecting the right surface with the front surface.

The description of the above configuration of main display surfaces and the operation modes thereof are only by way of example. In actual implementation, the same content can be displayed on the first display panel 01 and the second display panel 02 simultaneously, or different contents can be displayed on different display regions. The present invention is not limited thereto.

In actual implementation, in the above multi-facet display device according to the embodiments of present invention, the first display panel 01 and the second display panel 02 can include touch control display panel. Thus the user can perform respective operation by touching the functional buttons displayed on the display panel. The first display panel 01 and the second display panel 02 can include non touch control display panel. The present invention is not limited thereto.

In a case where the multi-facet display device is applied to a display wall, the first display panel and the second display panel can be transparent display panels. Thus some articles can be placed within the closed structure formed by the first display panel 01 and the second display panel 02 for exhibition, and related information such as the brief description of the exhibits can be displayed on the first display panel 01 and the second display panel 02 respectively, and can be browsed by using the touch control functions of the multi-facet display device. In a case where the multi-facet display device is applied to a cell phone, the first display panel and the second display panel are typically designed as non-transparent display panels.

In actual implementation, in the above multi-facet display device according to the embodiments of present invention, the first display panel 01 can for example be a LCD display panel, an OLED display panel or an electronic paper display panel. The respective second display panel 02 can also be a LCD display panel, an OLED display panel or an electronic paper display panel.

In addition, the first display panel 01 is subjected to a bending process. Therefore, the first display panel 01 has a flexible substrate. The flexible substrate can include a glass substrate. The function film layers on the substrate need also have respective flexibility, so that the first display panel 01 can be subjected to a bending process in a certain degree.

Furthermore, as illustrated in FIG. 1, the above multi-facet display device according to the embodiments of present invention can further include a first encasing plate 03 for closing a top of the closed structure and a second encasing plate 04 for closing a bottom of the closed structure. The first encasing plate 03 and the second encasing plate 04 each has a shape corresponding to the cross section shape of the top and bottom of the closed structure respectively, so that the top and bottom of the closed structure can be closed.

In actual implementation of fabricating the above multi-facet display device according to the embodiments of present invention, the first display panel 01 and the second display panel 02, the first display panel 01 and the first encasing plate 03, the first display panel 01 and the second encasing plate 04, the second display panel 02 and the first encasing plate 03, and the second display panel 02 and the second encasing plate 04 can be bonded by various methods such as pressing or adhering matching recesses and protrusions on respective parts, or screwing. The present invention is not limited thereto.

Figure 3:
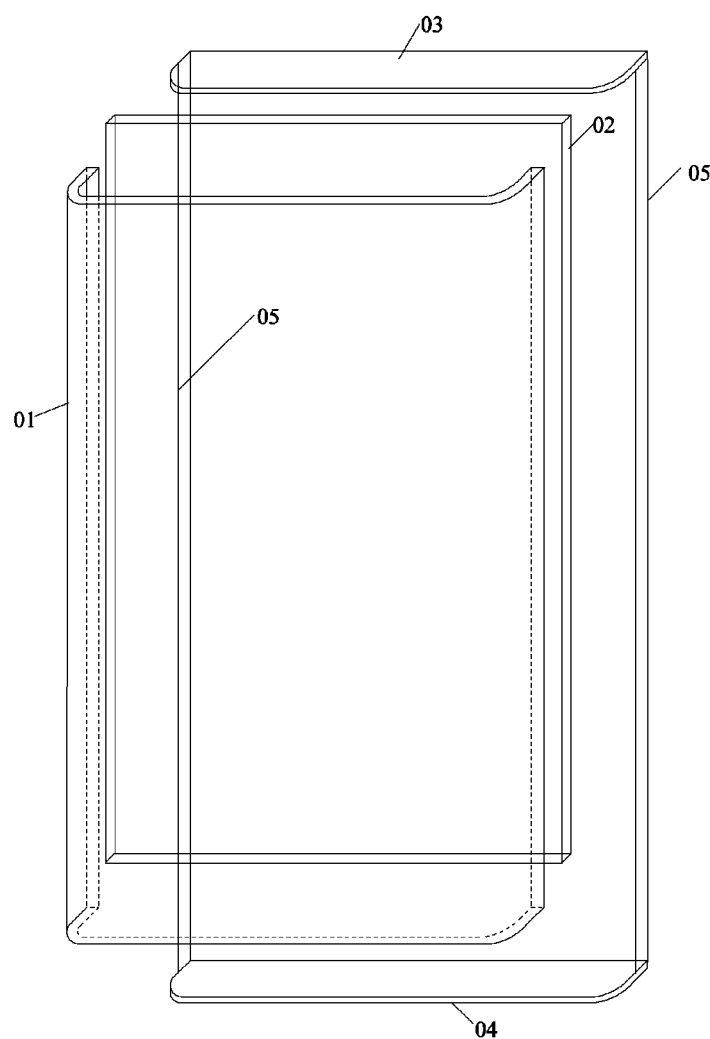
FIG. 3 is a structure exploded view of respective components in a multi-facet display device according to an embodiment of present invention.

In addition, in the above multi-facet display device according to the embodiments of present invention, in order to simplify the complexity of the structure, as illustrated in FIG. 3, the two side surfaces of the first display panel 01 and the two side edges of the second display panel 02 can be assembled via a third encasing plate 05 respectively.

Furthermore, the third encasing plate 05, the first encasing plate 03 and the second encasing plate 04 can also designed as an integral structure. Thus upon assembling the above multi-facet display device according to the embodiments of present invention, the integral structure, the first display panel 01 and the second display panel 02 can be directly assembled together.

Specially, the first display panel 01 and the second display panel 02 are assembled by the above method of pressing or adhering, which is beneficial to the frameless design at the joints of the first display panel 01 and the second display panel 02. That is, during the fabrication, the first display panel 01 and the second display panel 02 can be designed as frameless at the left and right side, so that the first display panel 01 and the second display panel 02 are frameless at least on the left and right side.

Furthermore, the first display panel 01 and the second display panel 02 typically each include a circuit board. In order to ensure the connection between the respective circuit board and the display panel in the first display panel 01 and the second display panel 02, a flexible electronic skin can be used. The flexible electronic skin can typically be made from rubber web-like conducting material. In case that the flexible electronic skin is used to connect the display panel and the circuit board, a complete frameless design including the top and bottom frame and the joints of the first display panel 01 and second display panel 02 on the side can be achieved, so that a true frameless annular display can be achieved in the final assembled multi-facet display device.

Figure 4:
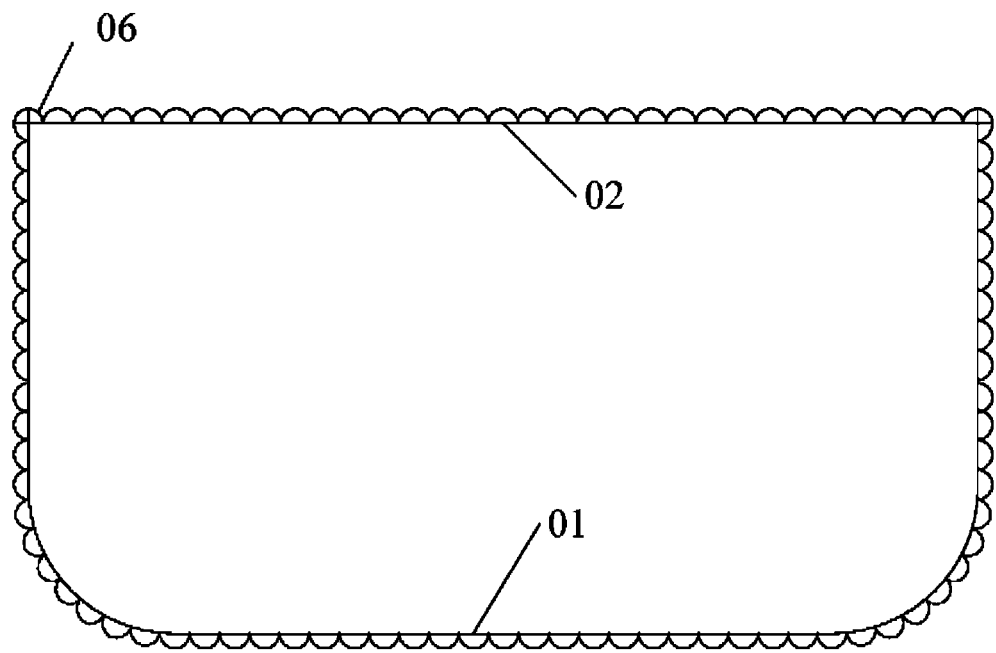
FIG. 4 is a schematic view of a multi-facet display device with transparent prism structure according to an embodiment of present invention.

Furthermore, the above multi-facet display device according to the embodiments of present invention can further include an optical component, so that the observer can not see the joints of the first display panel 01 and the second display panel 02 on the side visually. Specially, as illustrated in FIG. 4, the multi-facet display device can include a transparent prism structure 06 at a joint of the first display panel 01 and the second display panel 02, which can change the direction of the emitting lights. The transparent prism structure 06 can refract the otherwise normal emitting lights at the joints of the first display panel 01 and the second display panel 02 to other directions, so that the observer is unaware of the existence of the joints visually so as to achieve a visual frameless annular display effect.

It is noted that in a case where the first display panel 01 and the second display panel 02 are OLED display panels, the thin film packaging technology of OLED display panel can be used to achieve a physical frameless. In case where the first display panel 01 and the second display panel 02 are LCD display panels or electronic paper panels, due to limitation on the packaging technology of LCD display panels and electronic paper panels, the true physical frameless design cannot be achieved. Therefore some optical components such as the above transparent prism structure are used to achieve an optical frameless effect. In case that the first display panel 01 and the second display panel 02 are OLED display panels, some optical components can further be used to optimize the frameless effect.

In actual implementation, the transparent prism structure 06 can only be disposed at the joints of the first display panel and the second display panel on the side. The transparent prism structure 06 can alternatively be disposed at the entire outer surface of the first display panel and the second display panel. The present invention is not limited thereto.

Figure 5:
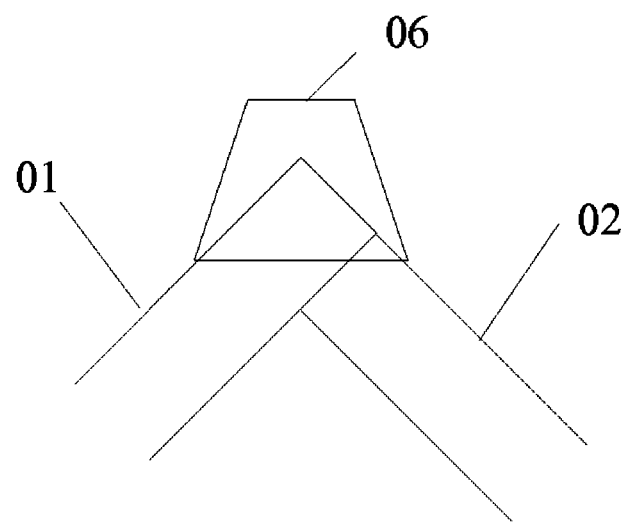
FIG. 5 is another schematic view of a multi-facet display device with transparent prism structure according to an embodiment of present invention.

In addition, the transparent prism structure 06 disposed at the joints of the first display panel 01 and the second display panel 02 can partially protrude out of the outer surface of the closed structure, i.e., the outer surface of the first display panel and the second display panel, as illustrated in the cross section view of FIG. 5. And the transparent prism structure 06 can have a cross sectional shape of arc (illustrated in FIG. 4) or a trapezoid (illustrated in FIG. 5) on a cross section which is perpendicular to the outer surface of said closed structure, i.e., the outer surface of the first display panel 01 and the second display panel 02, in order to change the light emitting direction.

Figure 6:
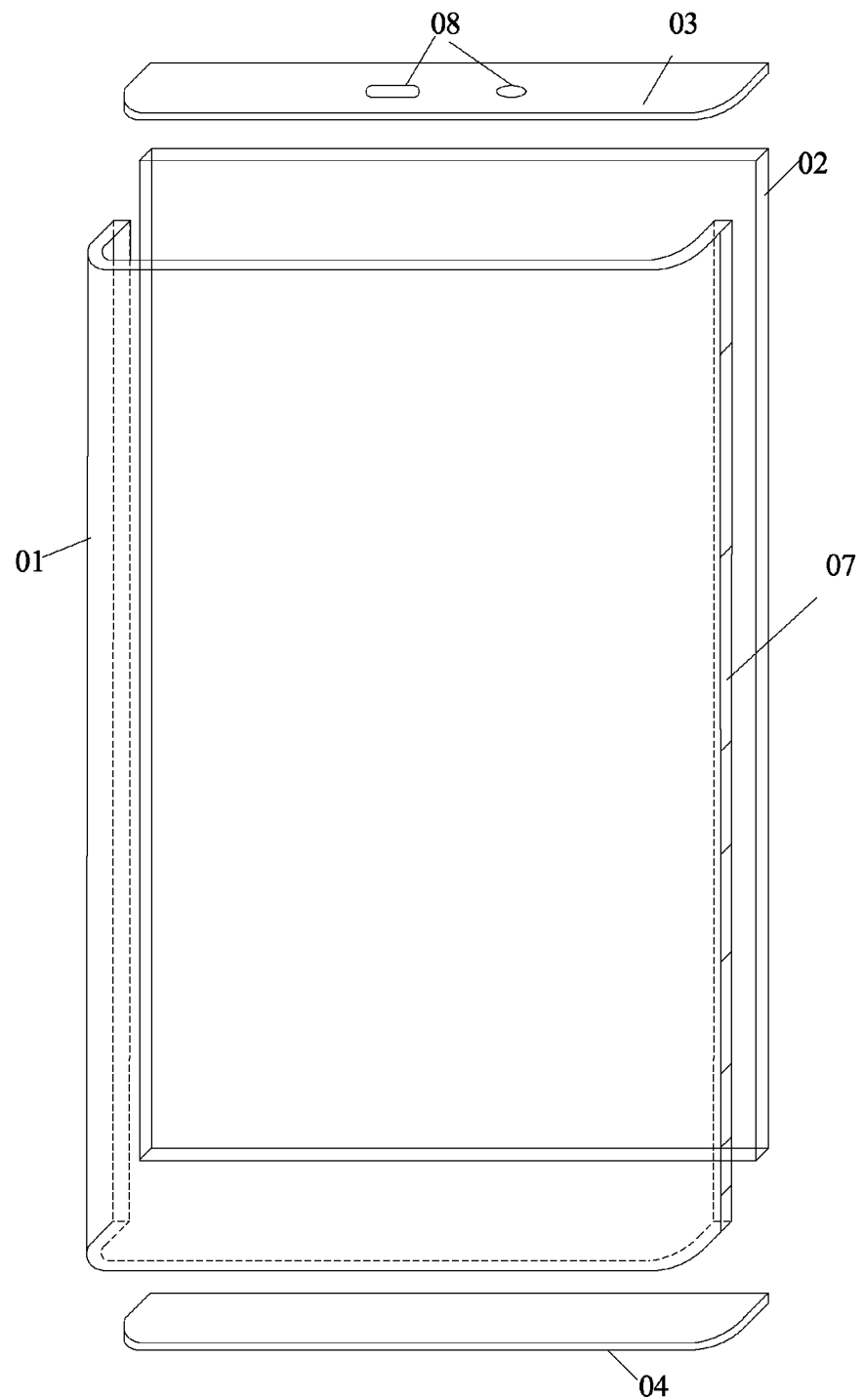
FIG. 6 is a structure exploded view of respective components in a multi-facet display device according to an embodiment of present invention.

Furthermore, as illustrated in FIG. 6, the above multi-facet display device according to the embodiments of present invention can further include at least one function slot 08 and/or physical functional button 07. Specially, the function slot 08 can be SD card slot, SIM card slot, USB slot, headset slot or charging slot, etc. The physical function button 07 can be a switch button, or a sound adjustment button, or a light intensity adjustment button. If there is some frame structure in the multi-facet display device according to the embodiments of present invention, the above function slot 08 and/or physical function button 07 can be at least disposed at one side surface of the first display panel 01, such as only on one side surface, or on both side surfaces. The present invention is not limited thereto. The function slot 08 and/or physical function button 07 can alternatively be disposed in a non-display region of the first display panel 01 and/or the second display region 02. If the multi-facet display device according to the embodiments of present invention is frameless, the above function slot 08 and/or physical function button 07 can be disposed on the surface of the first encasing plate 03 and/or the second encasing plate 04. As shown in FIG. 6, two function slots 08 are disposed on the first encasing plate 03, and multiple function buttons 07 are disposed on one side surface of the first display panel 01 and the second display panel 02.

Furthermore, in addition to the multi-facet display function, some other functions can also be added to the multi-facet display device according to the embodiments of present invention in order to increase the product value. For example, in actual implementation, the multi-facet display device according to the embodiments of present invention can further include a health monitoring unit. The health monitoring unit can detect the health level of human body, and perform the remote medical treatment, and display corresponding information on the display surface of the multi-facet display device.

If there is some frame in the multi-facet display device according to the embodiments of present invention, the health monitoring unit can be disposed on at least one side surface of the first display panel 01, such as only on one side surface, or on both side surfaces. The present invention is not limited thereto. The health monitoring unit can alternatively be disposed at a non-display region of the first display panel 01 and/or the second display panel 02. If the multi-facet display device according to the embodiments of present invention is frameless, the above health monitoring unit can be disposed on the surface of the first encasing plate 03 and/or the second encasing plate 04.

Typically, the health monitoring unit has a data acquisition unit and a data analysis and storage unit. Specially, the health monitoring unit can include an infrared detection unit and/or a minimally invasive detection unit having respective sensors. The infrared detection unit is configured for monitoring body temperature; and the minimal invasive detection unit is configured for monitoring blood sugar level.

Furthermore, in a case where the multi-facet display device according to the embodiments of present invention is applied to IT display product, TV, or cell phones and so on, the multi-facet display device can further include an image capturing device such as a camera disposed in the non-display region of the first display panel 01 and/or the second display panel 02, as well as a network connection device such as a blue tooth device. The present invention is not limited thereto.

The embodiments of present invention provide a multi-facet display device, which includes a first display panel and a second display panel. The two opposed side surfaces of first display panel bend toward the back of display region respectively so that the first display panel forms a U-shaped structure. The two opposed side surfaces of first display panel bending toward the back of display region are assembled with the two side edges of a second display panel respectively, thus forming a closed structure. The display surface of the multi-facet display device is the outer surface of the closed structure. In the multi-facet display device according to the embodiments of present invention, the first display panel with bending structure and the planar second display panel are assembled in a closed structure having image displaying surfaces in at least four directions of the closed structure. The display surfaces of the first display panel with U-shaped structure in three directions are connected as a curved surface via the arc surfaces. Compared with the multi-facet display device consisted of multiple planar display panels, the multi-facet display device according to present invention improve image continuity across respective display directions.

The foregoing detailed description of the invention has been presented for purposes of illustration and description. It is not intended to be exhaustive or to limit the invention to the precise form disclosed. Many modifications and variations are possible in light of the above teaching. The described embodiments were chosen in order to best explain the principles of the invention and its practical application to thereby enable the skilled in the art to best utilize the invention in various embodiments and with various modifications as are suited to the particular use contemplated. It is intended that the scope of the invention be defined by the claims appended hereto.

What is claimed is:

1. A multi-facet display device, comprising:
    a first display panel with a U-shaped structure, the first display panel comprising a display region with a planar structure, and two opposed side surfaces each connected with the display region via an arc surface; and
    a second display panel with a planar structure, wherein the two side surfaces of the first display panel are bonded with two side edges of the second display panel to form a closed structure having an outer surface as a display surface of the multi-facet display device, and wherein the first display panel and the second display panel are configured to display an image.

2. The multi-facet display device according to claim 1, further comprising:

a first encasing plate closing a top of the closed structure; and a second encasing plate closing a bottom of the closed structure.

3. The multi-facet display device according to claim 2, wherein the first display panel is bonded with the second display panel, the first display panel is bonded with the first encasing plate, the first display panel is bonded with the second encasing plate, and the second display panel is bonded with the second encasing plate, and the bonding is made by a method comprising pressing or adhering matching recesses and protrusions on respective parts, or screwing.

4. The multi-facet display device according to claim 3, further comprising a transparent prism structure at least disposed at joints between the side surfaces of the first display panel and side edges of the second display panel, the transparent prism structure being configured for changing directions of emitting lights.

5. The multi-facet display device according to claim 2, wherein the two side surfaces of the first display panel and the two side edges of the second display panel are assembled via a third encasing plate.

6. The multi-facet display device according to claim 5, wherein the third encasing plate, the first encasing plate and the second encasing plate are in an integral structure.

7. The multi-facet display device according to claim 6, further comprising a transparent prism structure at least disposed at joints between the side surfaces of the first display panel and side edges of the second display panel, the transparent prism structure being configured for changing directions of emitting lights.

8. The multi-facet display device according to claim 5, further comprising a transparent prism structure at least disposed at joints between the side surfaces of the first display panel and side edges of the second display panel, the transparent prism structure being configured for changing directions of emitting lights.

9. The multi-facet display device according to claim 2, further comprising at least one function slot and/or physical function button disposed on at least one side surface of the first display panel; or disposed at a non-display region of the first display panel and/or the second display panel; or disposed on a surface of the first encasing plate and/or the second encasing plate.

10. The multi-facet display device according to claim 9, further comprising a transparent prism structure at least disposed at joints between the side surfaces of the first display panel and side edges of the second display panel, the transparent prism structure being configured for changing directions of emitting lights.

11. The multi-facet display device according to claim 2, further comprising a health monitoring unit disposed on at least one side surface of the first display panel; or disposed at a non-display region of the first display panel and/or the second display panel; or disposed on a surface of the first encasing plate and/or the second encasing plate.

12. The multi-facet display device according to claim 11, wherein the health monitoring unit is an infrared detection unit for monitoring body temperature and/or a minimal invasive detection unit for monitoring blood sugar level.

13. The multi-facet display device according to claim 11, further comprising a transparent prism structure at least disposed at joints between the side surfaces of the first display panel and side edges of the second display panel, the transparent prism structure being configured for changing directions of emitting lights.

14. The multi-facet display device according to claim 2, wherein the first display panel is an LCD display panel, an OLED display panel or an electronic paper display panel; and the second display panel is an LCD display panel, an OLED display panel or an electronic paper display panel.

15. The multi-facet display device according to claim 14, wherein the first display panel and the second display panel are touch control display panels.

16. The multi-facet display device according to claim 2, further comprising a transparent prism structure at least disposed at joints between the side surfaces of the first display panel and side edges of the second display panel, the transparent prism structure being configured for changing directions of emitting lights.

17. The multi-facet display device according to claim 1, wherein the first display panel and the second display panel are at least frameless at joints between the side surfaces of the first display panel and side edges of the second display panel.

18. The multi-facet display device according to claim 1, further comprising a circuit board connected with the display surface of the multi-facet display device through a flexible electronic skin.

19. The multi-facet display device according to claim 1, further comprising a transparent prism structure at least disposed at joints between the side surfaces of the first display panel and side edges of the second display panel, the transparent prism structure being configured for changing directions of emitting lights.

20. The multi-facet display device according to claim 19, wherein the transparent prism structure at least partially protrudes out of the outer surface of the closed structure, and has an arc or trapezoid cross sectional shape on a cross section which is perpendicular to the outer surface of the closed structure.

* * * * *